United States Patent
Imam

(10) Patent No.: US 8,954,134 B2
(45) Date of Patent: Feb. 10, 2015

(54) LIGHT-GUIDED TRANSLUMINAL CATHETER

(75) Inventor: Farhad B. Imam, Brookline, MA (US)

(73) Assignee: Children's Medical Center Corporation, Boston, MA (US)

(*) Notice: Subject to any disclaimer, the term of this patent is extended or adjusted under 35 U.S.C. 154(b) by 1347 days.

(21) Appl. No.: 12/053,210

(22) Filed: Mar. 21, 2008

(65) Prior Publication Data
US 2008/0194973 A1 Aug. 14, 2008

Related U.S. Application Data

(63) Continuation-in-part of application No. 11/509,203, filed on Aug. 24, 2006, now abandoned.

(60) Provisional application No. 60/716,454, filed on Sep. 13, 2005, provisional application No. 61/024,666, filed on Jan. 30, 2008.

(51) Int. Cl.
*A61B 6/00* (2006.01)
*A61B 19/00* (2006.01)
*A61B 18/24* (2006.01)

(52) U.S. Cl.
CPC ............... *A61B 19/54* (2013.01); *A61B 18/24* (2013.01); *A61B 2019/5206* (2013.01); *A61B 2019/5445* (2013.01)
USPC ........................................................ 600/476

(58) Field of Classification Search
USPC ............ 600/424, 473, 476; 604/510; 128/899
See application file for complete search history.

(56) References Cited

U.S. PATENT DOCUMENTS

| | | | |
|---|---|---|---|
| 3,941,119 A | 3/1976 | Corrales | |
| 4,096,862 A | 6/1978 | DeLuca | |
| 4,248,214 A | 2/1981 | Hannah | |
| 4,444,185 A | 4/1984 | Shugar | |
| 4,567,882 A * | 2/1986 | Heller | ............ 600/249 |
| 4,729,068 A | 3/1988 | Ohe | |
| 4,747,833 A | 5/1988 | Kousai | |
| 4,771,782 A | 9/1988 | Millar | |
| 4,772,093 A | 9/1988 | Abele et al. | |

(Continued)

FOREIGN PATENT DOCUMENTS

| | | |
|---|---|---|
| EP | 0214712 | 3/1987 |
| EP | 1527748 | 5/2005 |

(Continued)

OTHER PUBLICATIONS

International Search Report for PCT/US06/34887.

(Continued)

*Primary Examiner* — Elmer Chao
(74) *Attorney, Agent, or Firm* — Fish & Richardson P.C.

(57) ABSTRACT

Generally, the present invention is directed to a light-guided catheter for direct visualization of placement through the skin. An embodiment of the invention includes a method for transcutaneous viewing and guiding of intracorporeal catheters into a body that comprises inserting a catheter into the body having at least one lumen and internally illuminating the catheter with light capable of propagating through the blood and tissue to an external viewer outside of the body. The illumination may be point source, continuous, single or multi wavelength. A method of treatment of blood conditions is also disclosed using direct placement of a photo treatment source in the blood stream.

28 Claims, 10 Drawing Sheets

(56) References Cited

U.S. PATENT DOCUMENTS

| | | | |
|---|---|---|---|
| 4,782,819 A | 11/1988 | Adair | |
| 4,850,358 A | 7/1989 | Millar | |
| 4,875,897 A | 10/1989 | Lee | |
| 4,898,175 A | 2/1990 | Noguchi | |
| 4,909,796 A | 3/1990 | Hagio | |
| 4,934,340 A | 6/1990 | Ebling | |
| 4,945,895 A | 8/1990 | Takai et al. | |
| 4,966,148 A | 10/1990 | Millar | |
| 5,005,180 A | 4/1991 | Edelman et al. | |
| 5,005,573 A | 4/1991 | Buchanan | |
| 5,005,592 A | 4/1991 | Cartmell | |
| 5,007,408 A | 4/1991 | Ieoka | |
| 5,019,040 A | 5/1991 | Itaoka et al. | |
| 5,054,500 A | 10/1991 | Littleford | |
| 5,125,404 A | 6/1992 | Kittrell et al. | |
| 5,131,380 A | 7/1992 | Heller et al. | |
| 5,142,155 A | 8/1992 | Mauze | |
| 5,178,616 A | 1/1993 | Uemiya | |
| 5,179,961 A | 1/1993 | Littleford | |
| 5,196,004 A | 3/1993 | Sinofsky | |
| 5,197,470 A | 3/1993 | Helfer et al. | |
| 5,217,456 A | 6/1993 | Narciso, Jr. | |
| 5,263,928 A | 11/1993 | Trauthen et al. | |
| 5,268,570 A | 12/1993 | Kim | |
| 5,290,275 A | 3/1994 | Kittrell et al. | |
| 5,306,244 A | 4/1994 | Shiber | |
| 5,370,640 A | 12/1994 | Kolff | |
| 5,415,654 A | 5/1995 | Daikuzono | |
| 5,417,688 A * | 5/1995 | Elstrom et al. | 606/64 |
| 5,423,311 A | 6/1995 | Snoke et al. | |
| 5,423,321 A * | 6/1995 | Fontenot | 600/476 |
| 5,448,582 A | 9/1995 | Lawandy | |
| 5,453,086 A | 9/1995 | Weber | |
| 5,456,680 A | 10/1995 | Taylor et al. | |
| 5,496,305 A | 3/1996 | Kittrell et al. | |
| 5,514,128 A | 5/1996 | Hillsman et al. | |
| 5,517,997 A | 5/1996 | Fontenot | |
| 5,522,389 A | 6/1996 | Fischer et al. | |
| 5,540,691 A | 7/1996 | Elstrom et al. | |
| 5,626,134 A * | 5/1997 | Zuckerman | 600/317 |
| 5,643,251 A | 7/1997 | Hillsman et al. | |
| 5,665,052 A | 9/1997 | Bullard | |
| 5,718,666 A * | 2/1998 | Alarcon | 600/249 |
| 5,728,079 A | 3/1998 | Weber | |
| 5,728,092 A | 3/1998 | Doiron et al. | |
| 5,733,277 A | 3/1998 | Pallarito | |
| 5,803,083 A | 9/1998 | Buck | |
| 5,879,306 A | 3/1999 | Fontenot et al. | |
| 5,902,247 A | 5/1999 | Coe | |
| 5,906,579 A | 5/1999 | Vander Salm et al. | |
| 5,907,395 A * | 5/1999 | Schulz et al. | 356/139.03 |
| 5,947,958 A | 9/1999 | Woodard et al. | |
| 5,951,482 A | 9/1999 | Winston | |
| 5,964,757 A | 10/1999 | Ponzi | |
| 5,993,382 A | 11/1999 | Pruitt | |
| 5,995,208 A | 11/1999 | Sarge et al. | |
| 5,995,866 A | 11/1999 | Lemelson | |
| 6,013,072 A | 1/2000 | Winston | |
| 6,022,334 A | 2/2000 | Edwards | |
| 6,048,349 A | 4/2000 | Winston | |
| 6,061,587 A | 5/2000 | Kucharczyk et al. | |
| 6,063,093 A | 5/2000 | Winston | |
| 6,081,741 A | 6/2000 | Hollis | |
| 6,095,990 A | 8/2000 | Parodi | |
| 6,113,588 A | 9/2000 | Duhaylongsod et al. | |
| 6,134,003 A | 10/2000 | Tearney et al. | |
| 6,146,409 A | 11/2000 | Overholt et al. | |
| 6,159,203 A | 12/2000 | Sinofsky | |
| 6,230,046 B1 | 5/2001 | Crane et al. | |
| 6,236,879 B1 | 5/2001 | Konings | |
| 6,246,901 B1 | 6/2001 | Benaron | |
| 6,306,097 B1 | 10/2001 | Park | |
| 6,332,089 B1 | 12/2001 | Acker et al. | |
| 6,364,874 B1 | 4/2002 | Bays | |
| 6,366,726 B1 | 4/2002 | Wach et al. | |
| 6,402,719 B1 | 6/2002 | Ponzi | |
| 6,419,653 B2 | 7/2002 | Edwards | |
| 6,445,943 B1 | 9/2002 | Ferre et al. | |
| 6,463,313 B1 | 10/2002 | Winston | |
| 6,475,226 B1 | 11/2002 | Belef et al. | |
| 6,519,485 B2 | 2/2003 | Wiesmann et al. | |
| 6,572,609 B1 | 6/2003 | Farr et al. | |
| 6,610,054 B1 | 8/2003 | Edwards | |
| 6,659,957 B1 | 12/2003 | Vardi | |
| 6,685,666 B1 | 2/2004 | Fontenot | |
| 6,701,176 B1 | 3/2004 | Halperin | |
| 6,704,590 B2 | 3/2004 | Haldeman | |
| 6,811,544 B2 | 11/2004 | Schaer | |
| 6,814,712 B1 | 11/2004 | Edwards | |
| 6,852,091 B2 | 2/2005 | Edwards | |
| 6,852,109 B2 | 2/2005 | Winston et al. | |
| 6,887,229 B1 | 5/2005 | Kurth | |
| 6,902,545 B2 | 6/2005 | Bertolero et al. | |
| 6,911,017 B2 | 6/2005 | Lee | |
| 6,915,154 B1 * | 7/2005 | Docherty et al. | 600/431 |
| 7,330,746 B2 * | 2/2008 | Demuth et al. | 600/322 |
| 7,773,749 B1 * | 8/2010 | Durst et al. | 380/54 |
| 7,917,193 B2 * | 3/2011 | Crane | 600/476 |
| 8,078,261 B2 | 12/2011 | Imam | |
| 2002/0013616 A1 * | 1/2002 | Carter et al. | 623/1.15 |
| 2002/0038120 A1 | 3/2002 | Duhaylongsod et al. | |
| 2002/0052597 A1 | 5/2002 | Duhaylongsod et al. | |
| 2002/0052621 A1 | 5/2002 | Fried | |
| 2002/0115922 A1 | 8/2002 | Waner et al. | |
| 2002/0123696 A1 | 9/2002 | Kokate et al. | |
| 2002/0127144 A1 | 9/2002 | Mehta | |
| 2002/0161290 A1 | 10/2002 | Chance | |
| 2003/0092995 A1 | 5/2003 | Thompson | |
| 2003/0114732 A1 | 6/2003 | Weblet et al. | |
| 2003/0130575 A1 | 7/2003 | Desai | |
| 2003/0187360 A1 | 10/2003 | Waner et al. | |
| 2003/0191379 A1 | 10/2003 | Benaron et al. | |
| 2003/0191398 A1 | 10/2003 | Motz et al. | |
| 2004/0019280 A1 | 1/2004 | Waner et al. | |
| 2004/0064021 A1 | 4/2004 | Pfeiffer | |
| 2004/0064022 A1 | 4/2004 | Korn | |
| 2004/0068178 A1 | 4/2004 | Govari | |
| 2004/0073120 A1 | 4/2004 | Motz et al. | |
| 2004/0092913 A1 | 5/2004 | Hennings et al. | |
| 2004/0093044 A1 | 5/2004 | Rychnovsky et al. | |
| 2004/0199052 A1 * | 10/2004 | Banik et al. | 600/142 |
| 2004/0215081 A1 * | 10/2004 | Crane et al. | 600/473 |
| 2004/0236231 A1 | 11/2004 | Knighton et al. | |
| 2005/0070788 A1 * | 3/2005 | Wilson et al. | 600/424 |
| 2005/0165462 A1 | 7/2005 | Bays et al. | |
| 2005/0240147 A1 | 10/2005 | Makower et al. | |
| 2006/0004317 A1 | 1/2006 | Mauge et al. | |
| 2006/0009785 A1 | 1/2006 | Maitland et al. | |
| 2006/0036164 A1 * | 2/2006 | Wilson et al. | 600/424 |
| 2006/0167439 A1 | 7/2006 | Kaiser | |
| 2006/0203508 A1 | 9/2006 | Lee | |
| 2007/0073160 A1 | 3/2007 | Imam | |
| 2007/0248307 A1 | 10/2007 | Page et al. | |
| 2008/0033519 A1 | 2/2008 | Burwell et al. | |
| 2012/0083689 A1 | 4/2012 | Imam | |

FOREIGN PATENT DOCUMENTS

| | | |
|---|---|---|
| WO | 98/40007 | 9/1998 |
| WO | 02/069784 | 9/2002 |
| WO | WO 02/103409 | 12/2002 |
| WO | 2005/057244 | 6/2005 |

OTHER PUBLICATIONS

International Search Report and Written Opinion for PCT/US2006/34887, mailed Feb. 21, 2007, 4 pages.

International Preliminary Report on Patentability for PCT/US2006/034887, mailed Mar. 18, 2008, 4 pages.

European Search Report for EP App. No. 06814290 mailed Sep. 21, 2010, 5 pages.

International Preliminary Report on Patentability for PCT/US2009/037927, issued Sep. 21, 2010, 10 pages.

(56) References Cited

OTHER PUBLICATIONS

International Search Report and Written Opinion for PCT/US2009/037927, mailed Jul. 23, 2009, 12 pages.
European Search Report issued in EP13190328 on Mar. 10, 2014 (7 pages).
USPTO Non-Final Office Action issued in U.S. Appl. No. 13/316,925 on Jun. 2, 2014 (10 pages).
Office Action in U.S. Appl. No. 11/509,203, mailed Sep. 14, 2009, 13 pages.
Office Action in U.S. Appl. No. 11/509,203, mailed Sep. 26, 2008, 10 pages.
Office Action in U.S. Appl. No. 12/636,975, mailed Dec. 20, 2010, 12 pages.
Office Action in European App. No. 06814290, dated Oct. 27, 2011, 3 pages.
Summons to attend oral proceedings in European App. No. 06814290, dated Mar. 14, 2013, 4 pages.

\* cited by examiner

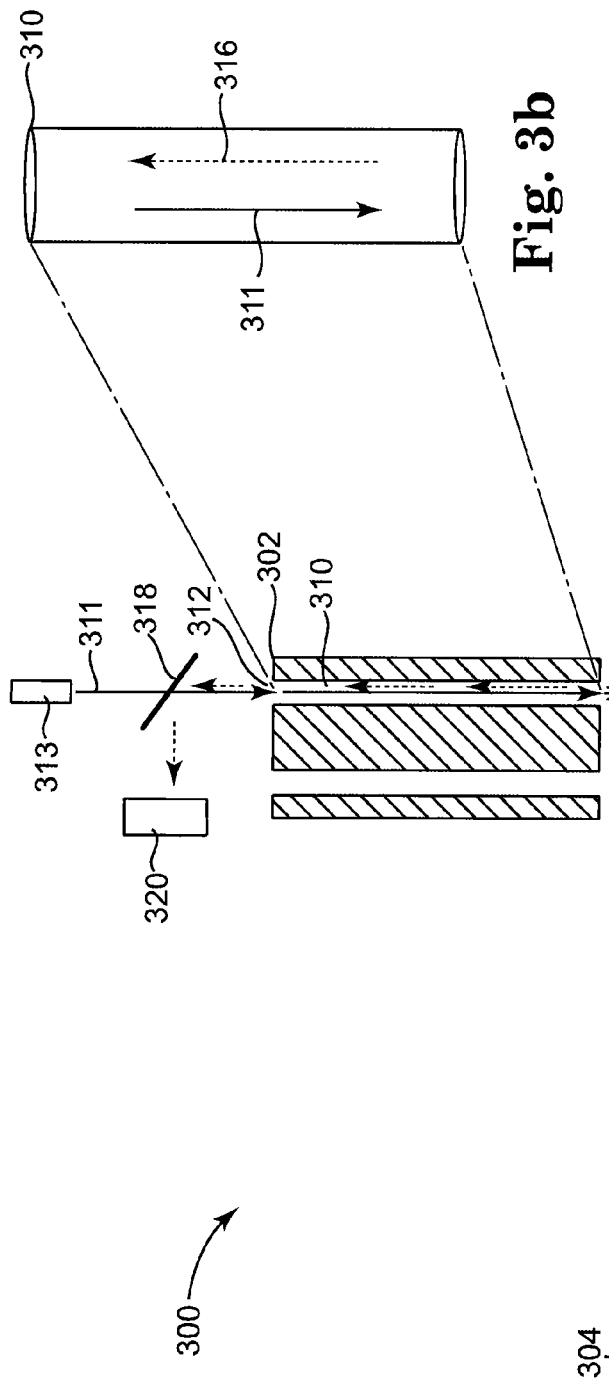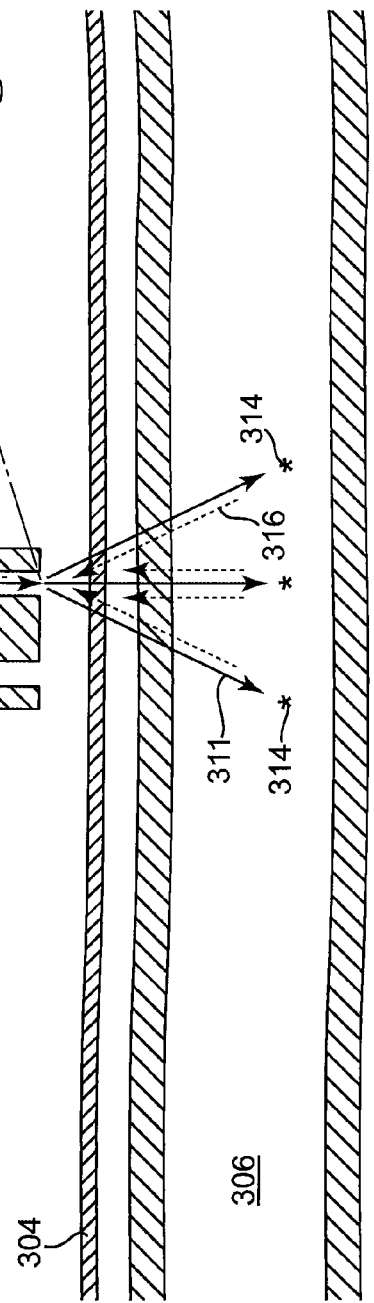

LIGHT-GUIDED TRANSLUMINAL CATHETER

CROSS-REFERENCE TO RELATED APPLICATIONS

The present application is a continuation-in-part of prior application Ser. No. 11/509,203 filed Aug. 24, 2006, now abandoned which claims the benefit of 60/716,454 filed Sep. 13, 2005 and 61/024,666 filed Jan. 30, 2008.

FIELD OF INVENTION

The present invention is directed generally to medical devices and more particularly to a light-guided catheter with inside-out transcutaneous illumination and visualization of placement through the skin including a method to locate non-visible blood vessels for catheterization.

BACKGROUND

Generally, to insert a catheter into a blood vessel, the vessel is initially identified via aspiration by a syringe with an attached hollow needle by a technique commonly referred to as the Seldinger technique. When blood is drawn into the syringe, this indicates that the vessel has been found. The syringe is then disengaged from the needle and the needle lumen is occluded to prevent a possible air embolism and/or to prevent excessive bleeding. Thereafter, confirmation of needle placement in the vein or artery can be assured by haemodynamic monitoring or checking for pulsatile blood flow. Then, a thin guide wire is introduced, typically through the syringe needle or other introducer device, into the interior of the blood vessel. The needle/introducer device is then withdrawn leaving the guide wire within the vessel, wherein the guide wire projects outwardly beyond the surface of the skin.

At this point, several options are available to a physician for catheter placement. The simplest is to pass the catheter directly into the blood vessel directly over the guide wire. The guide wire is then withdrawn, leaving the catheter in position within the vessel. Correct catheter tip placement may then be verified by x-ray procedures. However, this technique is only possible in cases where the catheter is of a relatively small diameter and not significantly larger than the guide wire. If the catheter to be inserted is significantly larger than the guide wire, a dilator device may be first passed over the guide wire to enlarge the insertion hole. The catheter is then introduced over the dialator/guide wire, and the guide wire and dilator are withdrawn.

The technique may be rather routine and straightforward in cases where the patient's blood vessel is near the surface of the skin and is directly visible. If one is inserting a catheter into such vessels, the path of the catheter quickly becomes invisible without special equipment like x-ray and radio opaque coating on the catheter. For newborns use of x-ray is often not advised. Fortunately the elderly and newborns have fairly translucent skin and this fact is taken advantage of with the present invention. Even more, once the elusive vessel is found, the insertion and steering of the catheter is usually a blind procedure with verification of correct catheter tip placement only confirmed after the fact by radiographic methods.

Given this, there is a need for a technique continuously in real time to visualize and/or identify the relative location of non-visible blood vessels for initial catheter entry and subsequent real-time visualization while guiding the catheter for correct tip placement. Furthermore, there are circumstances where other tubes may need to be placed within the body and be guided without the need to special technologies such as x-rays.

Finally, it may be useful to have a technique which can locate blood vessels by non interventional detection of blood constituents.

SUMMARY OF THE INVENTION

Generally, the present invention is directed to medical devices and more particularly to a light-guided catheter with inside-out transcutaneous illumination and visualization of placement through the skin for the purpose of allowing real-time visual guidance, including a method to locate non-visible blood vessels for catheterization.

One particular embodiment of the invention is directed to a method for transcutaneous viewing and guiding of intracorporeal catheters into a body that comprises inserting a catheter into the body having at least one lumen and internally illuminating the catheter with light capable of propagating through the blood and tissue to an external viewer outside of the body.

Another embodiment of the invention is directed to a method for transcutaneous viewing and guiding of intracorporeal catheters into a body that comprises inserting a catheter into the body having at least one lumen and inserting into the lumen a source of illumination capable of propagating through the blood and tissue to an external viewer outside of the body.

Another embodiment of the invention is directed to a method for transcutaneous viewing and guiding of intracorporeal/intraarterial catheters wherein the internally illuminated catheter emits light of a first color and further includes the step of inserting into the catheter lumen a second source of illumination of a second color different from the first color, both of the colors being capable of propagating through blood and tissue to an external viewer outside of the body, whereby the location of each illumination source can be discerned from outside the body.

Another embodiment of the invention is directed to a method for transcutaneous viewing and guiding of intracorporeal catheters wherein the internally illuminated catheter is made of a material opaque to visible light and the light emitting device extends beyond the distal end of the catheter.

Another embodiment of the invention is directed to a method of locating non-visible intracorporeal/blood vessels for catheterization comprising illuminating candidate locations with light capable of inducing fluorescence from blood constituents and detecting fluorescent response from the blood constituents thereby selecting the potential site for catheterization based upon detection of a predetermined fluorescent signal.

Another embodiment of the invention is directed to a transcutaneously viewable catheter comprising a tubular member having an insertable end and a first channel along the length of the catheter. The catheter has a removable illumination source in said channel having at least an illuminated end, the source being configured to be extendible through said channel and beyond said end so that when the source is inserted into the channel, the illumination is visible outside the body, and the end thereof can be visually located.

Another embodiment of the invention is directed to a transcutaneously viewable catheter wherein the tubular member is substantially opaque to light from the illumination source; so that when the removable source is extended beyond the end of the member, the illumination is visible outside the body.

Another embodiment of the invention is directed to a transcutaneously viewable catheter wherein the tubular member is partially transparent to light emitted by the illumination source; so that when the illumination source reaches the end of tubular member, an observer can detect the difference in level or color of light transmission as the illumination source exits the tubular member.

Another embodiment of the invention is directed to a transcutaneously viewable catheter wherein the illumination source is leaky and emits light along at least a portion of its length, whether discrete or continuous.

Another embodiment of the invention is directed to a transcutaneously viewable catheter wherein the illumination source emits more light at its end than elsewhere therealong, so that it is possible to easily discern its path and end from outside the body.

Another embodiment of the invention is directed to an apparatus for locating substantially non-visible intracorporeal/blood vessels for catheterization comprising a tubular member having an insertable end and a channel along the length thereof. The apparatus has a removable illumination source insertable in the channel having an illuminated end configured to be extendible through the channel. The illumination source is capable of emitting light of predetermined optical wavelengths to excite fluorescence from blood constituents including an optical channel to receive fluorescence from blood constituents and an optical detector coupled to the optical channel to measure the fluorescence from the blood constituents. This embodiment could be incorporated into all other embodiments for facilitation of initial vessel identification and placement prior to catheter insertion and final optimization of final tip placement.

Another embodiment of the invention is directed to an apparatus for locating substantially non-visible intracorporeal/blood vessels for catheterization wherein an appropriate illumination source would be used, such as a low-loss fiber optic conductor or light-emitting diode.

Another embodiment of the invention is directed to an apparatus for locating substantially non-visible intracorporeal/blood vessels for catheterization wherein the optical channel simultaneously delivers the illumination energy to excite fluorescence and receives fluorescence from blood constituents.

Another embodiment of the invention is directed to an apparatus for locating substantially non-visible intracorporeal/blood vessels for catheterization wherein the optical components include a separator, such as but not limited to a dichroic mirror, to separate illumination and fluorescence signals prior to the optical detector.

Another embodiment of the invention is directed to a transcutaneously viewable catheter comprising a tubular member having an insertable end and a first channel along the length of the catheter, with a first optic having an end and being formed within the tubular member and running substantially the length thereof. At least a portion of the first optic is leaky and an illumination source is connected to the optic to provide illumination at least along a portion of the length of the catheter with an optimized color of light so that the illumination is visible outside the body.

Another embodiment of the invention is directed to a transcutaneously viewable catheter comprising a tubular member having an insertable end and a channel along the length of the catheter, with a first optic embedded within the tubular member and running substantially the length thereof and a second optic inserted into the catheter channel and running substantially the length thereof. At least a portion of both optics are leaky and separate illumination sources of distinguishable colors or intensities are connected to each optic so that when both are illuminated the location of the end of the second optic can be distinguished from the first optic.

Another embodiment of the invention is directed to a transcutaneously viewable catheter comprising a tubular member having an insertable end and a channel along the length of the catheter, with a first optic embedded within the tubular member and running substantially the length thereof and a second optic inserted into the catheter channel and running substantially the length thereof. At least a portion of both optics are leaky, the second optic being leaky only near its end, and separate illumination sources of distinguishable colors are connected to each optic so that when both are illuminated the location of the end of the second optic can be distinguished from the first optic.

Another embodiment of the invention is directed to a transcutaneously viewable catheter comprising a tubular member having a first and second optic embedded within the tubular member and running along the length of the catheter. At least a portion of both optics are leaky, the second optic being leaky proximate its end, and separate illumination sources of distinguishable colors are connected to each optic so that when both are illuminated the location of the end of the second optic can be distinguished from the first optic.

Another embodiment of the invention is directed to a transcutaneously viewable catheter comprising a tubular member having an insertable end and a first channel along the length of the catheter, with a first optic having an end and being formed within the tubular member and running substantially the length thereof. At least a portion of the first optic is leaky and an illumination source is connected to the optic to provide illumination at least along a portion of the length of the catheter with a predetermined color of light so that the illumination is visible outside the body. The catheter further includes an enlongated radio opaque element having an end and being insertable through the first channel, so that the location of the end of the elongated element can be distinguished from the first optic and detected from outside the body.

Another embodiment of the invention is directed to a transcutaneously viewable catheter comprising a tubular member having a first and second optic embedded within the tubular member and running along the length of the catheter. At least a portion of both optics are leaky, the second optic being leaky proximate to its end, and separate illumination sources of distinguishable colors are connected to each optic so that when both are illuminated, the location of the end of the second optic can be distinguished from the first optic.

The catheter further includes an enlongated radio opaque element having an end and being insertable through the first channel. In this manner, the location of the end of the elongated element can be detected either visually via fluorescence using the light-emitting optic, or by radio detection (X-ray fluoroscopy techniques) if the optic has been removed.

In another embodiment, there is disclosed a transcutaneously viewable catheter having a tubular member having an insertable end and a first channel along the length of said catheter; and an optionally removable illumination source having a proximal end and a tip at its distal end, said source being insertable into said channel having at least an illuminated end and a plurality of points of illumination along the length thereof, said points being spaced apart and separated by non-illuminated segments, so that when said source is inserted into the channel, the illumination is visible outside the body, and the end thereof can be visually located.

A further embodiment includes the source being configured to be extendible through said channel and beyond said end.

A further embodiment include the spaced apart plurality of illumination points being progressively closer together as they approach the tip.

A further embodiment has the points of illumination including a fiber optic having a plurality of deformations therein.

A further embodiment has the deformations at least partially filled with a translucent lens material.

A further embodiment has the lens material include suspended reflective particles.

In a further embodiment the particles are powdered silver.

In a further embodiment, the points include a lens dome filler which fills the deformations and creates a diffusing or focusing lens thereon.

In a further embodiment the deformations are cuts into the fiber optic and wherein the cuts are progressively deeper as the cuts approach the tip.

In a further embodiment the points of illumination are modulated so that their on-cycle time is less than 100 percent.

In a further embodiment the points are modulated so that they are illuminated progressively or sequentially toward the distal end.

In a further embodiment the points are illuminated with greater intensity progressively toward the distal end.

In a further embodiment the points are modulated at one frequency and the illumination point at the tip is modulated at a second frequency different from the first.

In a further embodiment the points of illumination include simultaneous radiation of at least two different colors of light.

In a further embodiment each of the two colors of light has different absorption rates in tissue, so that the depth of placement of the point of light can be determined by the combination of color at different depths.

In a further embodiment one color is progressively stronger at the distal end and the other color is progressively stronger at the proximal end.

Another embodiment shows a transcutaneously viewable catheter having a tubular member having an insertable end and at least one channel along the length of said catheter; and an illumination source having a proximal end and a tip at its distal end, said source wound around said member along a helical path from proximal to distal end; plurality of points of illumination along the length of said illumination source, said points being spaced apart and separated by non-illuminated segments and a translucent sheath over said source.

In a further embodiment the points illuminate said catheter periodically at varying points around the circumference of the tubular member, so that all sides of the catheter are illuminated by a plurality of points from proximal to distal ends.

In a further embodiment further including a heat sink in said tubular member and extending generally the length thereof, to reduce heat generated by said illumination source.

In a further embodiment the deformations are cuts burned into the fiber optic.

In a further embodiment the tip is illuminated by a point unidirectional point source, so that the orientation of the tip can be know by visualization of the point source by the user.

In a further embodiment the unidirectional point source is an LED in said tip pointing orthogonally to the longitudinal direction of the catheter.

In a further embodiment the unidirectional point source includes a plurality of unidirectional point sources around the circumference of the tip pointing orthogonally to the longitudinal direction of the catheter.

A further embodiment is disclosed which is a method of treating a patient with a blood related condition which is treatable by external photo therapy, having the steps of, inserting a catheter into a blood vessel in the patient, causing the catheter to illuminate at a light wavelength and intensity required to affect the blood condition, terminating the illumination at the end of treatment, and withdrawing the catheter In a further embodiment the blood condition is bilirubin and the catheter is placed into a blood vessel which receives most of the body's blood flow.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 3A shows a side-view of a multi-lumen catheter device with a fiber optic inserted into a working channel of the catheter wherein the catheter device is delivering optical radiation to the patient's blood vessel and receiving a fluorescent signal back from chemistry constituents within the patient's blood.

FIG. 3B is an enlargement of the fiber optic device depicted in FIG. 3A, highlighting the counter propagating excitation and fluorescent optical signals traversing the fiber optic device.

FIG. 10a is view of another embodiment with a fiber optic.

FIG. 10b is a lateral view of the embodiment is FIG. 10a.

Figure 1:
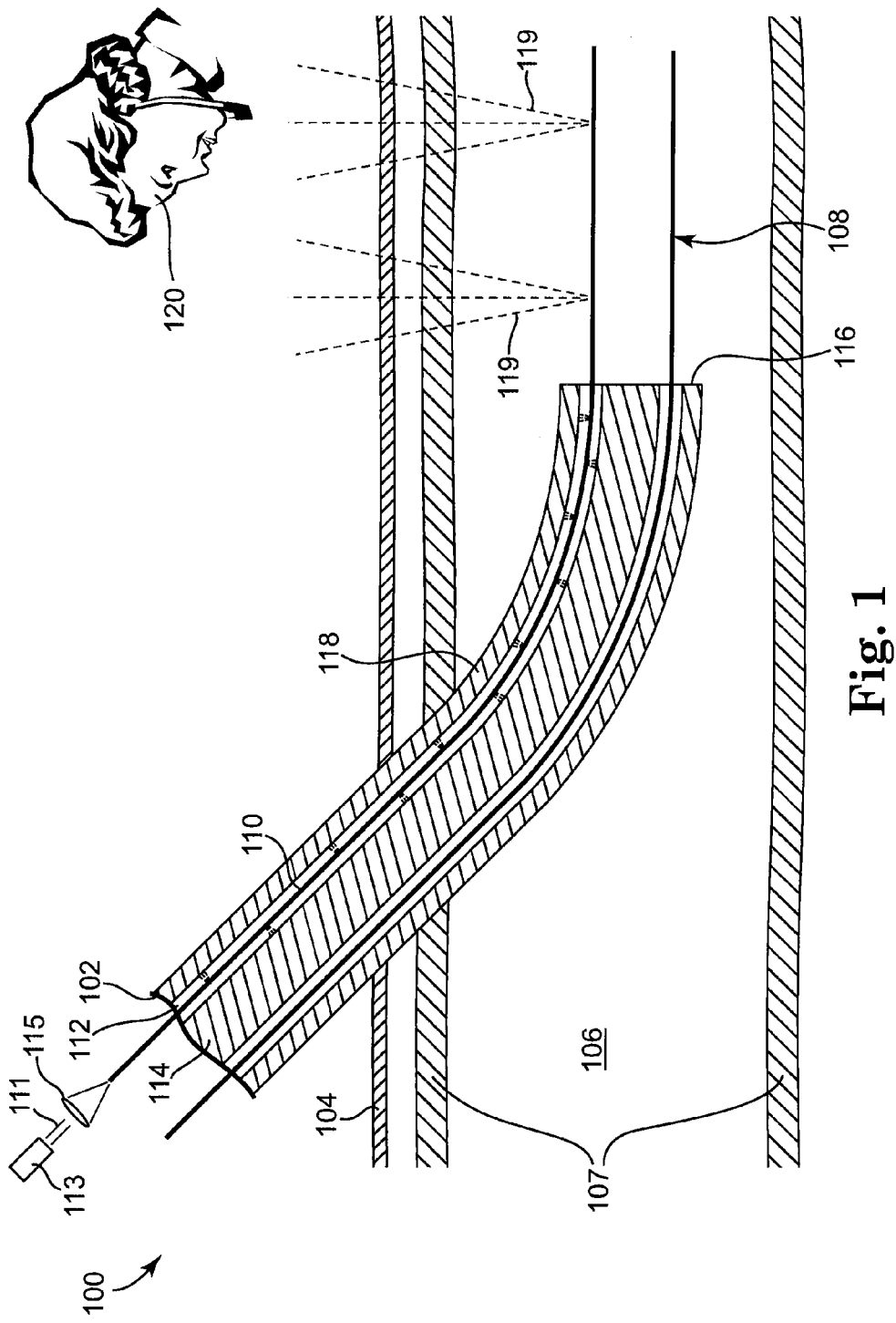
FIG. 1 shows a schematic representation of an optically opaque multi-lumen catheter device inserted into a patient's blood vessel with a fiber optic device inserted into a working channel of the catheter providing inside-out transcutaneous illumination near the distal end of the catheter.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

In general, the present invention is directed to medical devices and more particularly to a light-guided catheter for direct visualization of placement through the skin. The catheter may be placed intracorporeal (inside the body) by any of the catheterization techniques known to those skilled in the art, and the invention includes, but is not limited to intravenous, intraarterial, or intraluminal placement of the catheter.

One embodiment of a light-guided transluminal catheter device 100 is depicted schematically in FIG. 1. A multi-lumen catheter 102 is shown having been inserted through the patient's skin 104 and into the blood vessel lumen 106 over the guidewire 108 via the usual insertion techniques (e.g., the Seldinger technique mentioned earlier). A similar catheter without initial guidewire may also be inserted directly through the lumen of the puncturing needle. This is commonly done in the case of peripherally-inserted central catheters (PICC) inserted in an extremity such as the arm or leg and threaded all the way to the heart.

Prior to insertion into the patient's blood vessel lumen 106 through blood vessel wall 107, the surgeon may insert a fiber optical device 110 into an available working channel 112 of the multi-lumen catheter 102. Alternatively, the fiber optic device 110 may be used in lieu of the guidewire following the Seldinger technique described earlier. In this approach, the fiber optic device 110 is inserted through the hypodermic needle and the catheter 102 is introduced into the patient's blood vessel by sliding the catheter over the fiber optic device 110. The fiber optical device 110 may comprise a plurality of "leaky" optical fibers or other light radiating structures which may extend from the exposed end 114 of the catheter 102 to slightly protruding outward from the distal end 116 of the catheter 102 into the patient's blood vessel lumen 106. By leaky, we refer to those optical fibers which radiate or scatter light energy radially outward continuously along at least a portion of the length, i.e. the lateral surface of the fiber. In the preferred embodiment, light emitted would preferably be in the visible light range so that special detection equipment is not required. Illuminating at least a portion of the length of the catheter is desirable, for example, when inserting the catheter it may be highly advantageous to "see" the lateral surface of the catheter when navigating a bend or curve in the patient's blood vessel, which is not uncommon when inserting an intracardiac or "central" catheter from a peripheral location, as in PICC (peripherally inserted central catheter) placement at a distal extremity and threaded toward the heart. In this configuration, the physician may get direct visual confirmation that the catheter is proceeding smoothly "around the bend" without complications. This should be interpreted to mean that a portion of the lateral surface of the catheter, which will be inserted into the body, is capable is emitting illumination. Illumination-merely at the tip of the catheter would not be considered to be a portion along the length or lateral surface thereof since the tip is not reasonably considered to be "a length". Likewise, the entire length thereof should be interpreted broadly so as to encompass less than every millimeter of the length, but much of the length which is inserted into the body so that the full pathway can be detected. Light emitting devices 113 may be optically coupled to the optical fibers 110 by means well known in the art of optical communications. For example, light output 111 from the light emitting devices 113 may be coupled into the optical fiber 110 via a focusing lens 115 or other light coupling components. The light emitting devices 113 may be chosen from the list of lasers, light emitting diodes, tungsten-halogen lamps or other suitable light sources with appropriate optical wavelength outputs to be visible by the naked eye or an opto-electronic detector. In the case where opto-electronic detectors are used which may be sensitive to non-visible wavelengths (infrared, ultraviolet, etc.) appropriate alternative light sources and optical fibers may be utilized to generate, guide, and ultimately detect non-visible wavelengths emanating from the fibers.

Note that this embodiment may be made with a non removable light source (fiber, LED, etc) which is manufactured under the external sheath of the catheter but does not form a removable pathway/lumen. This would still allow a single or dual (or more) lumen construction, but the light source would be permanent. In this embodiment, the catheter can be made with a smaller diameter if desired.

With respect to the wavelengths of light that have worked best with the catheters, many of them are suitable. The main differences lie in the penetrance of immediate and adjacent tissues, in which the red wavelengths seem to be the most effective (~625-680 nm), but 532 nm (green) also works sufficiently. This general wavelength has the advantage of minimizing the amount of scattering and provides for more precise catheter localization as would the red range at, for example, 5 milliwatts (mw) of power.

Therefore, preferred embodiments might include green (532 nm) and/or red (635 nm) wavelength light sources coupled to the optic, which in preliminary experiments in rabbits and neonatal humans have been able to penetrate >1 cm of tissue and therefore would be visible to the naked eye at depths of up to 1 cm below the skin surface with relatively low light power (<5 mw).

In short, visible light is highly advantageous because no special detection equipment is needed other than perhaps dimming of the ambient room light, which is already routinely practiced in the ICU environment with traditional venous transilluminators to identify vessels for venipuncture and/or arterial puncture.

In the embodiment depicted in FIG. 1, the outer surface/protective sheath 118 of the multi-lumen catheter device 102 may be optically opaque so that only optical radiation 119 emanating from that portion of the optical fiber protruding from the distal end of the catheter 116 may propagate outward through the luminal blood 106/skin 104 regions ultimately to the surgeon's eyes 120 for direct viewing of the in-dwelling location of the catheter tip region 116 (this region being defined as the tip itself and a portion of the catheter extending away from the tip so that a sufficient portion of the catheter can be easily detected. By illuminating only the tip, (essentially a point source) the possibility of an error in detection or reading is increased. This is avoided by illuminating a region adjacent the tip simultaneously. The light emitting devices 113 may be operated continuously, intermittently, modulated (periodic or non periodic), or in pulsating/strobing fashion to facilitate visibility through the luminal blood 106/skin 104 regions. Given this, the physician may visually track the location of the distal end region of the catheter 116 as the catheter is maneuvered further upstream in the patient's blood vessel lumen 106 toward the ultimate targeted location. Alternatively, the physician may insert the fiber optical device 110 after the catheter 102 is initially inserted into the patient's blood vessel lumen 106 and guide the catheter 102 by viewing the illuminated distal tip 116 as mentioned above.

Figure 2:
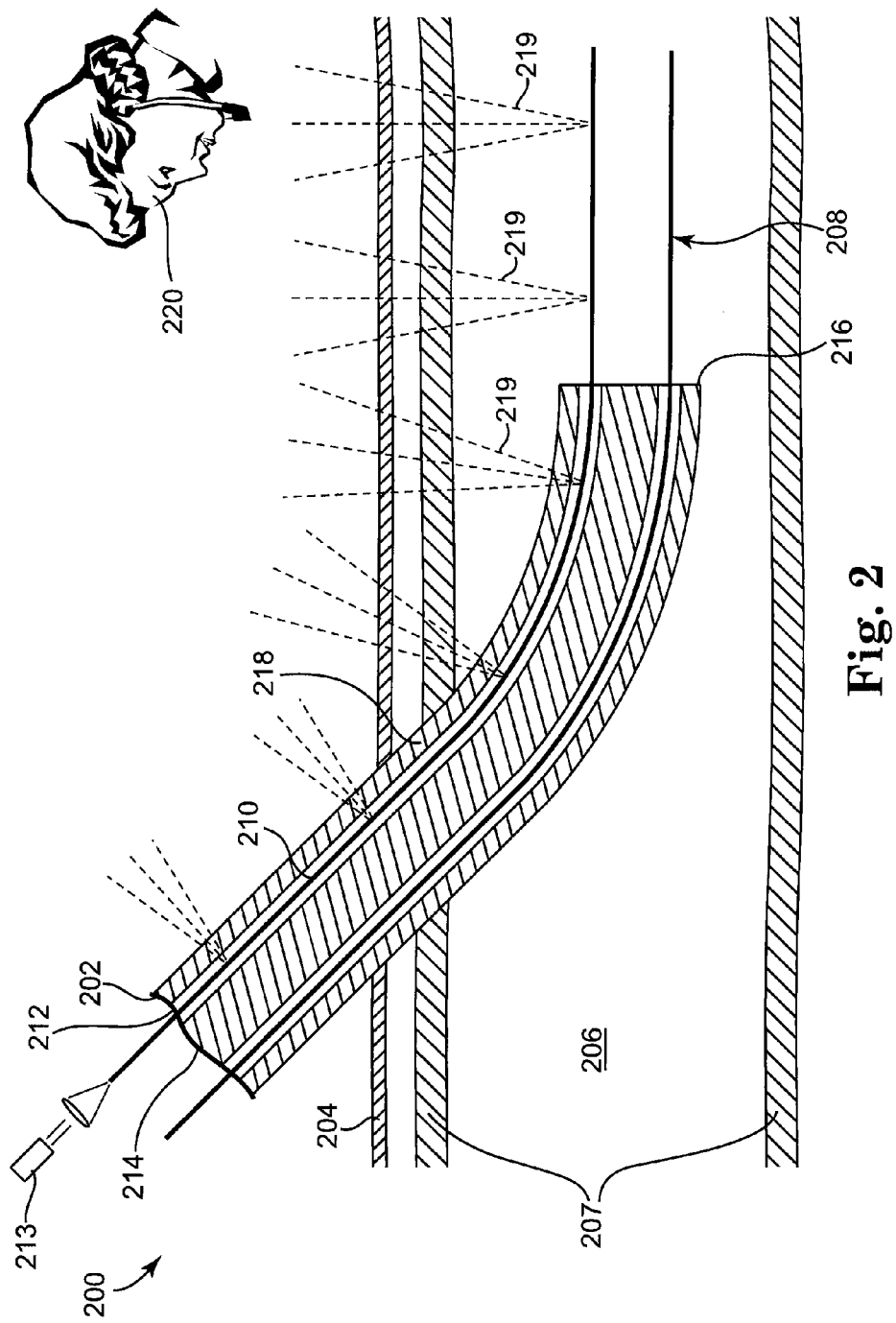
FIG. 2 shows a schematic representation of an optically transparent multi-lumen catheter device inserted into a patient's blood vessel with a fiber optic device inserted into a working channel of the catheter providing inside-out transcutaneous illumination along the length of the catheter.

An alternative embodiment 200 of the present invention is depicted schematically in FIG. 2. A multi-lumen catheter 202 is shown having been inserted through the patient's skin 204 and into the blood vessel 206 over the guidewire 208 via the usual insertion techniques (e.g., the Seldinger technique mentioned earlier).

Prior to insertion into the patient's blood vessel 206, the surgeon may insert a fiber optical device 210 into an available working channel 212 of the multi-lumen catheter 202. The fiber optical device 210 may consist of a plurality of "leaky" optical fibers or other light radiating structures which may extend from the exposed end 214 of the catheter 202 to slightly protruding outward from the distal end 216 of the catheter 202 into the patient's blood vessel 206. By leaky, we refer to those optical fibers which radiate or scatter light energy radially outward continuously along the length of the fiber. Light emitting devices 213 may be optically coupled to the optical fibers 210 by means well known in the art of optical communications. The light emitting devices 213 may be chosen from the list of lasers, light emitting diodes, tungsten-halogen lamps or other suitable light sources with appropriate optical wavelength outputs to be visible by the naked eye.

In the embodiment depicted in FIG. 2, the outer surface 218 of the multi-lumen catheter device 202 may be partially, segmentally, or entirely optically transparent so that optical radiation 219 emanating from the optical fiber may propagate outward along the entire length of the fiber/catheter through the blood 206/skin 204 regions ultimately to the surgeon's eyes 220 for direct viewing of the in-dwelling location of the catheter 202. The outer surface 218 may also modify the intensity, scatter, or wavelength of light passing through it such that the observer or detector would be able to discern the portion of the optic fiber extruded past the catheter tip from the potion lying within it. Given this, the physician may visually track the location of the entire length of the catheter 202 as the catheter is maneuvered further upstream in the patient's blood vessel 206 toward the ultimate targeted location. Alternatively, the physician may insert the fiber optical device 210 after the catheter 202 is initially inserted into the patient's blood vessel 206 and guide the catheter 202 by viewing the illuminated catheter as mentioned above. In an alternative embodiment, the fiber optic device 210 may be inserted into an available working channel 212 of the multi-lumen catheter 202 as before, however, in this case prior to patient insertion the fiber end-face may be withdrawn a sufficient distance back into the distal end 216 of the catheter such that only the lateral surface 218 of the catheter is illuminated. This configuration may eliminate the possibility of the fiber end-face irritating the wall of the patient's blood vessel as the catheter is being inserted, while still illuminating through the lateral surface of a translucent or otherwise non-opaque catheter, the lateral surface 218 of the catheter 202 during insertion and final placement.

In situations where the physician threading the catheter is particularly interested in the location of the catheter tip, the physician may utilize two individual optical fibers 210 to achieve this result. For example, one fiber may be either be pre-loaded into the catheter 202 flush with the distal end 216 of the catheter 202 or the fiber may be embedded in the wall of the catheter 202 terminating at the distal end 216 of the catheter 202. This fiber may be "leaky" along its length and when coupled with a blue LED light source 213, for example, it may illuminate the entire sidewall of the catheter 202 with a blue tint, seen transcutaneously. A second "non-leaky" optical fiber may be inserted into a working lumen of the catheter 202 and may be coupled to a green LED. As the second fiber is inserted into catheter 202 and slightly beyond the distal end 216 of the catheter 202 the transition from blue to green seen transcutaneously may serve as a marker identifying the location of the distal tip 216 of the catheter 202. Of course, different color light sources than the blue/green pair outlined above may be utilized to achieve similar results, wherein in all cases it is preferred that the light sources generate light visible to the naked eye.

An alternative embodiment to locate the distal tip 216 of the catheter 202 incorporates embedding two separate optical fibers in the wall of the catheter 202. Similar to the above embodiment, the first optical fiber may be embedded in the wall of the catheter 202 terminating at the distal end 216 of the catheter 202. The first fiber may be "leaky" along its length and when coupled with a blue LED light source 213, for example, it may illuminate the entire sidewall of the catheter 202 with a blue tint, seen transcutaneously. A second "non-leaky" (i.e., optical energy only radiating from the distal end) fiber may also be imbedded in the wall of the catheter 202 terminating approximately an inch from the distal end 216 of the catheter 202 and may be coupled to a green LED. In this configuration, the transition from a pure blue transcutaneous tint to a blue/green mixture may identify the location of the distal end region 216 of the intracorporeal catheter 202. As before, different choices for the light sources may lead to acceptable alternative color combinations for transcutaneous viewing such as blue/white, green/white, yellow/blue and the like.

Another embodiment of the present invention comprises the combination of a fiber-illuminated catheter used in tandem with a traditional radio-opaque wire used in X-ray fluoroscopy. In this embodiment, a single or multiple lumen catheter may have the illuminating and/or radio-opaque fiber either embedded in the wall of the catheter or inserted in an available catheter lumen as before. The radio-opaque wire may be inserted into a vacant catheter lumen or inserted into the same lumen as the illuminating fiber. The illuminating fiber itself may also be radio-opaque (though another embodiment and includes a radio-opaque fiber which will both provide propagation of light when connected to a source of illumination, but also be visualized on radiographs). In this configuration, the physician may switch back and forth between the two approaches as necessary. For example, an initial entry into the radial artery (arm) destined for the cardiac region may proceed as follows. Initial entry and threading in the arm may be guided directly by transcutaneous viewing of the fiber-illuminated catheter as outlined before. Upon entry into the chest cavity region, the physician may choose to switch to standard X-ray fluoroscopy when and if the visibility of the fiber-illumination becomes too faint to discern.

Another embodiment of the present invention encompasses a dual-purpose function of the illuminating fiber. In this embodiment the illuminating optical fiber is inserted into an available lumen and illuminates the distal end of the catheter as previously outlined. In addition, the fiber may have optically excited chemical sensors attached to the distal end of the fiber. For example, fluorescent dyes sensitive to the dissolved oxygen in blood (sometimes referred to as the partial pressure of oxygen in blood and designated as $pO_2$) are well known and historically have been encapsulated in a polymer membrane attached to the distal end of the sensing fiber. Similarly, additional fluorescent dyes have been demonstrated to respond to the dissolved carbon dioxide in blood ($pCO_2$) as well as the acidity (pH) of blood. The trio above, pO2, pCO2, and blood pH are commonly referred to as a "blood gas" measurement in a hospital setting.

A detailed explanation of the mechanism involved for optically sensing "blood gases" by way of fluorescent chemical sensors/dyes attached to the distal end of an optical fiber can be found in U.S. Pat. No. 5,672,515 titled "Simultaneous Dual Excitation Single Emission Fluorescent Sensing Method For pH and $pCO_2$" which is incorporated herein by reference. The additional ability to measure one or more of the "blood gases" while simultaneously viewing the illuminated catheter transcutaneously may allow the physician sufficient information to ascertain whether the catheter has been threaded into arterial or mixed venous blood, given that typical blood gas measurements for venous blood is discernibly different than arterial values.

The above embodiments may also be particularly useful in the placement of peripherally-inserted central catheters (commonly referred to as PICC lines), as well as umbilical artery and vein catheters used in the neonatal intensive care units. PICC lines are commonly introduced into the patient's arm or leg through the lumen of the puncturing needle and threaded all the way to the patient's heart. The PICC lines are subject to being misrouted when inserted and guided (threaded) blindly, and with direct transcutaneous viewing of the catheter while threading, this may be alleviated. The direct transcutaneous viewing of the catheter while threading may be ideal for newborn infants with inherently thin skin, and may also be applicable to a large segment of the adult population, especially the elderly.

An alternative embodiment of the present invention is depicted schematically in FIGS. 3A and 3B. FIG. 3A shows a catheter 300 configured to function as an artery or vein-finder device to optically locate blood vessels which may not be visible directly by the unaided eye. A side view of a multilumen catheter 302 is shown in contact with a patient's skin 304 directly over the patient's blood vessel 306. An optical fiber 310 has been inserted into an available working channel 312 of the catheter 302. The optical fiber 310 may be similar to those currently used in optical communications (i.e., "non-leaky" in contrast to the "leaky" fibers depicted in FIGS. 1 and 2) with the ability to waveguide light over long distance with minimal loss out the lateral surface. Light emitting devices 313 may be optically coupled to the optical fibers 310 by means well known in the art of optical communications. The light emitting devices 313 may be chosen from the list of lasers, light emitting diodes, tungsten-halogen lamps or other suitable light sources with appropriate optical wavelength outputs to excite optical fluorescence from chemistries in the underlying blood vessel. In this configuration, the catheter 302 with inserted optics to excite and receive fluorescent signals from chemistries in the underlying blood vessel, may serve as an artery/vein finder to identify the correct location for the initial needle stick (first step in Seldinger technique or in PICC placement) to facilitate the process of eventually placing the catheter in-dwelling. A detailed explanation of the optical technique is described below.

Naturally occurring chemistries in human blood are well known to fluoresce when excited (illuminated) at a particular wavelength corresponding to the absorption band of that chemistry. During the subsequent fluorescence process (which usually occurs on the order of a few nanoseconds after absorbing the illuminating optical energy), the molecule responds by emitting optical energy at a longer wavelength (i.e., lower energy state) than the exciting/illuminating energy. For example, blood constituents bilirubin and carotenoid chromophores are known to fluoresce in the spectral region near 450 nanometers when optically excited (illuminated) at 340 nanometers. Fluorescence form these molecules may be used to locate the position of underlying blood vessels as follows. The light source 313 in FIG. 3A may be chosen to emit optical radiation 311 near 340 nanometers (corresponding to the absorption band of bilirubin for example) which may be coupled into optical fiber 310 which guides the optical radiation 311 to the patient's skin surface 304. The optical radiation 311 may penetrate through the patient's skin 304, traverse the blood vessel wall, enter the patient's blood stream and eventually interact (be absorbed by) a bilirubin molecule 314 present in the patient's blood stream. Thereafter, the bilirubin molecule 314 may re-radiate a fluorescent optical signal 316 (see the expanded view of the fiber 310 shown in FIG. 3B), a portion of which may be coupled back into the optical fiber 310 and guided back toward the light source 313. The returning fluorescent signal 316 may be reflected by partial mirror 318 to optical detector 320 which may have optical filters embedded to only respond to the 340 nanometer signal indicative of bilirubin/blood fluorescence. In this configuration, the optical detector 320 would receive the maximum fluorescent signal back from the bilirubin molecule 314, when the catheter 302/fiber 310 device is directly placed over the underlying blood vessel 306.

Figure 4:
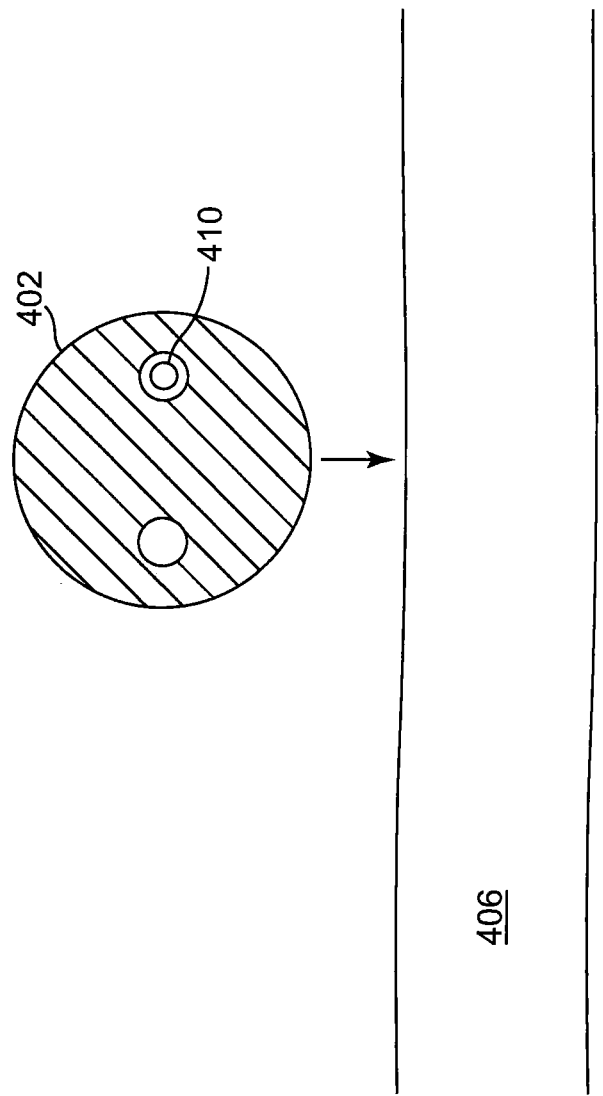
FIG. 4 is a top view (looking down) of the catheter device shown in FIG. 3A showing the catheter device laterally displaced from the underlying patient's blood vessel.
Figure 5:
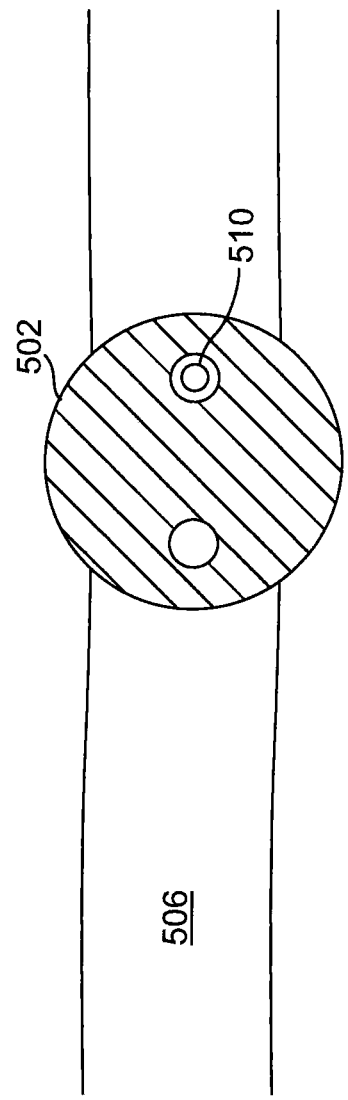
FIG. 5 is a top view (looking down) of the catheter device shown in FIG. 3A showing the catheter device directly centered over the underlying patient's blood vessel.

For example, FIG. 4 shows a top view (looking down on the device depicted in FIG. 3) of the catheter 402 depicting the fiber 410 inserted in the working channel on the right hand side of the catheter 402. The catheter is shown displaced vertically, i.e., off-set from directly over the underlying blood vessel 406, and as such the fluorescent signal 316 (from FIG. 3) captured by the optical fiber 410 will be relatively small. However, when the catheter is translated down directly over the blood vessel (see FIG. 5), the catheter 502 can be manually positioned back-and-forth until a maximum fluorescent signal 316 (FIG. 3) is detected by the optical detector 320 signifying the blood vessel 506 has been located. This process can be repeated at several adjacent points to delineate the course of the vessel subcutaneously and further aid with correct insertion.

As noted above, the present invention is directed generally to medical devices and more particularly to a light-guided catheter with inside-out transcutaneous illumination and visualization of placement through the skin including a method to locate non-visible blood vessels for catheterization.

Other embodiments of the present invention are also contemplated.

Figure 8:
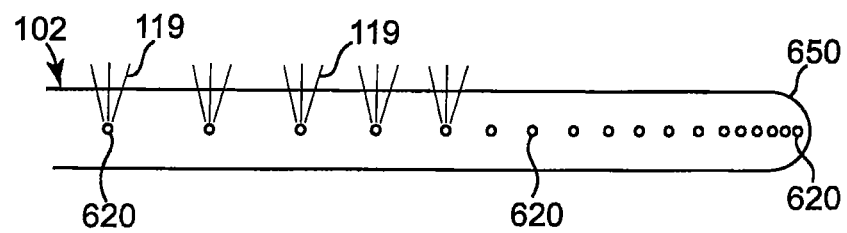
FIG. 8 is a schematic view of a point source illumination system with points being increasingly closer together as they approach the tip.
Figure 9:
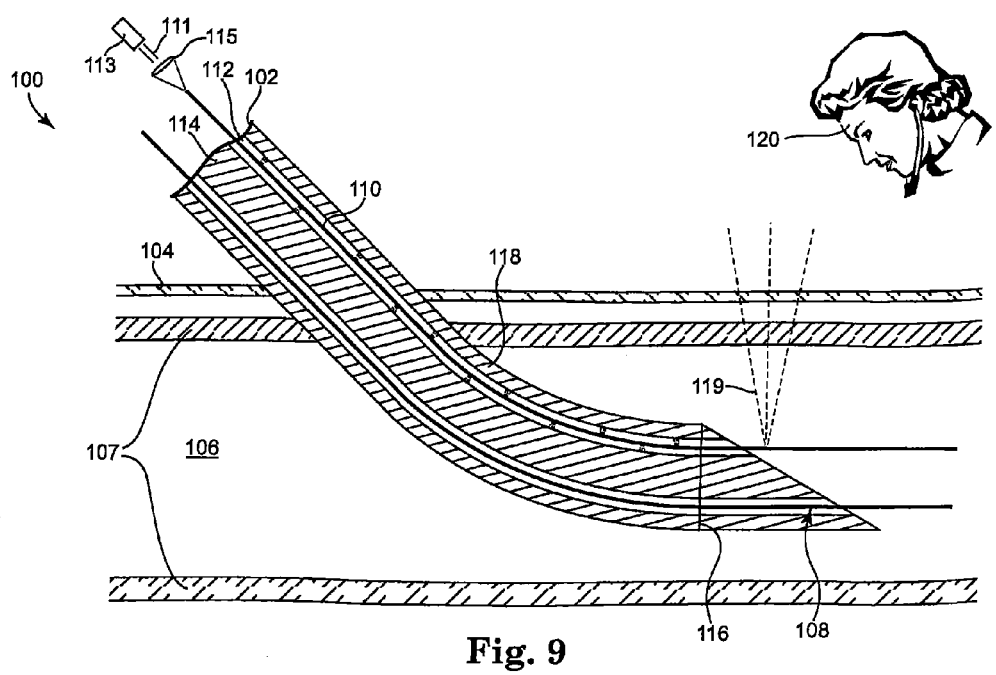
FIG. 9 is a view of a catheter with a wedge shaped tip.

As shown in FIG. 2, the illumination source (fiber optic, diodes, etc.) may provide discontinuous illumination in the form of point sources 219 spaced apart along the length of the catheter. There may also be strips (vs. points) of light or other discontinuous variations. The discontinuities may vary across the length of the catheter. For example, spacing between points of illumination may be progressively less (or greater) when approaching the tip to help locate the tip. See FIG. 8 which shows a schematic view of a point illumination scheme with a plurality of points 620 with their illumination pattern 119 as they approach tip 650. The illumination of such points may also be pulsed, intermittent or sequential from end to end, to help locate the tip. In this embodiment, their inter-point spacing is progressively smaller as it approaches the tip. It can also be the opposite. Either way, it makes it easier to determine the direction of the catheter and location of the tip by making the distance between any two points unique, so that should only a portion of the catheter be visible, it would be able to determine which section(s) by the distance between any two visible points.

The advantage of such point sources is that they will require less energy and also generate less heat than continuously leaky fibers, which may be of particular concern. Point source illumination is possible with side emitting LEDs, scoring of fiber optics to make them leaky at certain points and orientations, polymer fibers deformed at points, or by other means.

One strategy is to "deform and scatter" light uniformly across all points of emission using plastic fibers with heat deformation. Deformations can be made by numerous means including mechanical or electrical and chemical cutting into the optic. A heated wire or laser can for example make a precision cut into the surface. Scoring of the fiber may be accomplished by many cutting means including heated filaments, chemical etching and/or lasers. One preferred solution is accomplished with a small tungsten wire which burns small defects into the fiber. Another is a pin point laser burn.

The cuts may be uniform or they may be progressively greater/lesser approaching the distal end, thereby clearly indicating direction toward the tip.

To enhance viewability of deformations, the cuts/notches can be filled with transparent or translucent material which will form a dome or lens. In addition, the dome may be formed of a suspension of reflective materials (such as silver or aluminum powder) which later hardens. The reflective suspension will cause uniform scatter of light for optimal viewability.

Using a stronger laser with approximately 3-5 mW per single point of emission on the optical fiber allows multiple points to be readily visible (e.g., a 17 mW laser for a fiber with 4 emission points).

Another method for scoring is using optical fibers of 1 mm, 0.75 mm, or 0.5 mm diameters which are then scored at specific points and then filled at those defects with a silver powder lacquer (or other translucent filler material with light scattering property) to cause a directed light cone/dome (whereas mere translucent material makes a more symmetrical cone of light), or a lens like structure, to emanate from each of the multiple points. Using a slotted fixture to hold the fiber it is possible to expose only the desired surface areas and of the fiber to specific depths so as to reproduce depth of the scoring of the fiber at each point. In addition, scoring can be progressively deeper as one moves toward the distal end of the fiber to allow a similar amount of light emission from each point along the fiber, since the amount of light reaching each successive point becomes attenuated. The scoring defects farther along ("downstream") the fiber must be larger or deeper to reach a similar brightness as the previous ones, in which more total light was flowing through the fiber. Therefore, the fixture can be customized to different cut depths along the fiber course.

Figure 10:
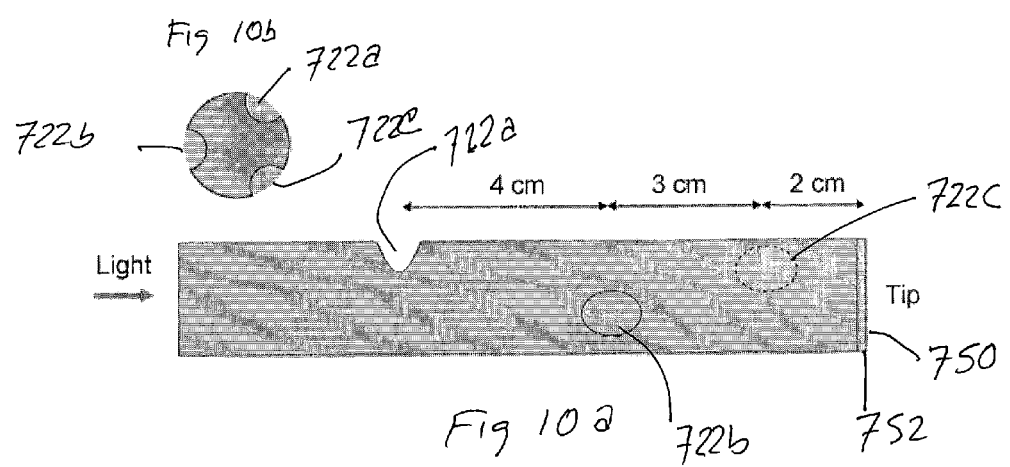
Figure 11:
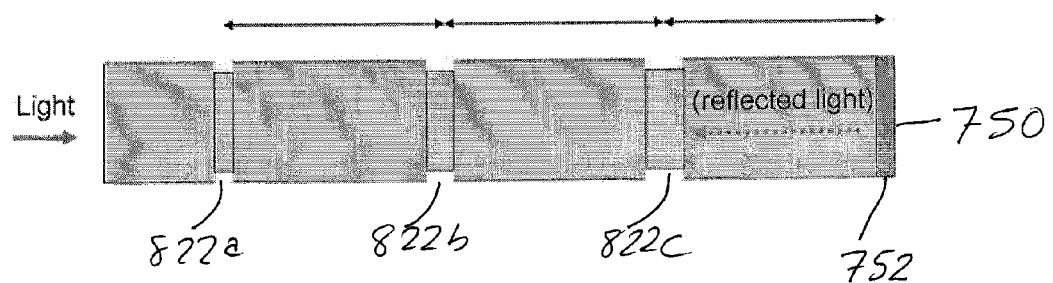
FIG. 11 is a view like FIG. 10b, except a further embodiment with circumferential scoring.

FIGS. 10a-10b and 11 illustrate various embodiments which can be used to provide orthogonal illumination of the catheter's position. FIGS. 10a-10b illustrate an embodiment of the catheter which has a plurality of point deformations in the periphery of the fiber optic. The catheter 110 may contain a fiber optic, or the fiber optic may be hollow (in effect being the catheter) or some other combination which provides a light path along the length thereof.

In order to ensure that the light exits the catheter/fiber optic in a way which is visible to an external viewer (person) who is essentially orthogonal to the catheter path, there must be means cause increased scattering of light within the optic in an orthogonal direction. The embodiment of FIGS. 10a-10b use point deformations 722a-c in the circumferential surface of the fiber optic. In the preferred embodiment, these deformations are spaced around the exterior at about 120 degrees circumferential rotations and helical down the length thereof and repeat periodically not unlike the embodiment in FIGS. 6-9. Also like the embodiment in FIG. 8, it is desirable to space the deformations succeedingly closer together (or farther apart) as indicated by the linear measurements shown in FIG. 10b. Of course the spacing shown is only one possibility.

The tip of the optical fiber 750 may be cut flat as shown or other shapes such as 45 degree wedge (FIG. 9) or rounded (FIG. 8) or other. In any configuration, it may be desirable to add a (partial) mirrored finish 752 on the interior wall facing the end of the fiber optic. This will reflect a portion of the light reaching the end. The advantage of this is to provide additional light to the deformations most adjacent the end, which would otherwise have the least light transmission.

In the case of a wedge shaped tip, there is a further advantage that the wedge (hypotenuse) surface will be directional and allow the user to know which way the catheter tip is pointing and thus make threading of the catheter through the body easily detectable.

The deformations 722a-c may also be filled with a translucent filler material and made flat to mate with the remaining optic periphery or with a semicircular dome as explained for other embodiments. The filler material may be plastic, lacquer, UV glue or other fluid hardening material. It may also be mixed with silver or reflective flakes in cause increased scatter. The depth of the deformations should preferably not exceed the radius of the optical fiber as it may weaken it. In this embodiment, the external diameter of the fiber is 750 micrometers and the deformation is 300 micrometers.

FIG. 11 illustrates a variation on FIGS. 10a-b. Instead of point deformations, the deformation is completely circumferential grooves/deformations 822a-822c. The grooves or bands can be formed in the same manner as mentioned above or the point deformations. They may be filled or coated with a transparent or translucent filler after cutting. The advantage of this structure is that light will radiate in all directions at each periodic point.

To further reduce heat, emission points (stripes, etc) can be modulated to shift position, much as a display screen saver shifts location to prevent screen burn in. The average increase in tissue temperature along the catheter can thereby be reduced to negligible levels. Furthermore, the modulation will help the viewer see the path of the lights. The modulation can be, for example, directional (the series of point/stripe illumination beginning at one end of the catheter, and ending at the other, usually the tip) so as to aid the viewer in finding the path even when there are visual "drop outs" (i.e., portions of the catheter that are occluded for whatever reason).

The directional modulation can be of increasing intensity as it approaches the tip for example.

The tip itself can be especially modulated at a different pulse frequency from other points to accentuate that it is the end point.

Modulation can be made so that the duty cycle on-time is less than 100%, probably closer to 30-50%. The modulation can be in terms of progressive frequency toward one end and can have progressive illumination/brightness. It can also be modulated with two frequencies at different portions of the catheter, or one frequency at the tip and another elsewhere.

This concept can also be combined with the use of two colors of illumination. By varying the intensity of each color along the length of the catheter, the view can better know how far along the length he/she is viewing. For example, a green/blue combination can dominate in green at one end and dominate in blue at the other, for example.

Another purpose of using two color simultaneously is to get a sense of depth (depth of field). Since each color is absorbed and/or scattered differently by tissue, there will be a color shift as the catheter goes deeper under more tissue or other obstructions. If one color is more effectively absorbed by tissue, the initial color combination will shift toward the color that is less absorbed and/or scattered. For example, equal green and red light sources would be seen initially as a yellow light, which would become visibly more orange-red as the light source traveled deeper under more tissue since green light is less able to penetrate tissue than red light.

It is also possible to have one color predominate (stronger) at the distal end and there predominate at the proximal end and become progressively weaker toward its opposite end, but not for the purpose of depth perception.

Point illumination can be achieved by discrete LED (diodes) embedded in the lumen/catheter at fixed points or by modification of the fiber optic to emit point light. Side emitting fibers can be used.

In addition to point illumination, it is possible to have both point and continuous illumination. The points would either be brighter or modulated in some way (flashing, for example).

Figure 6:
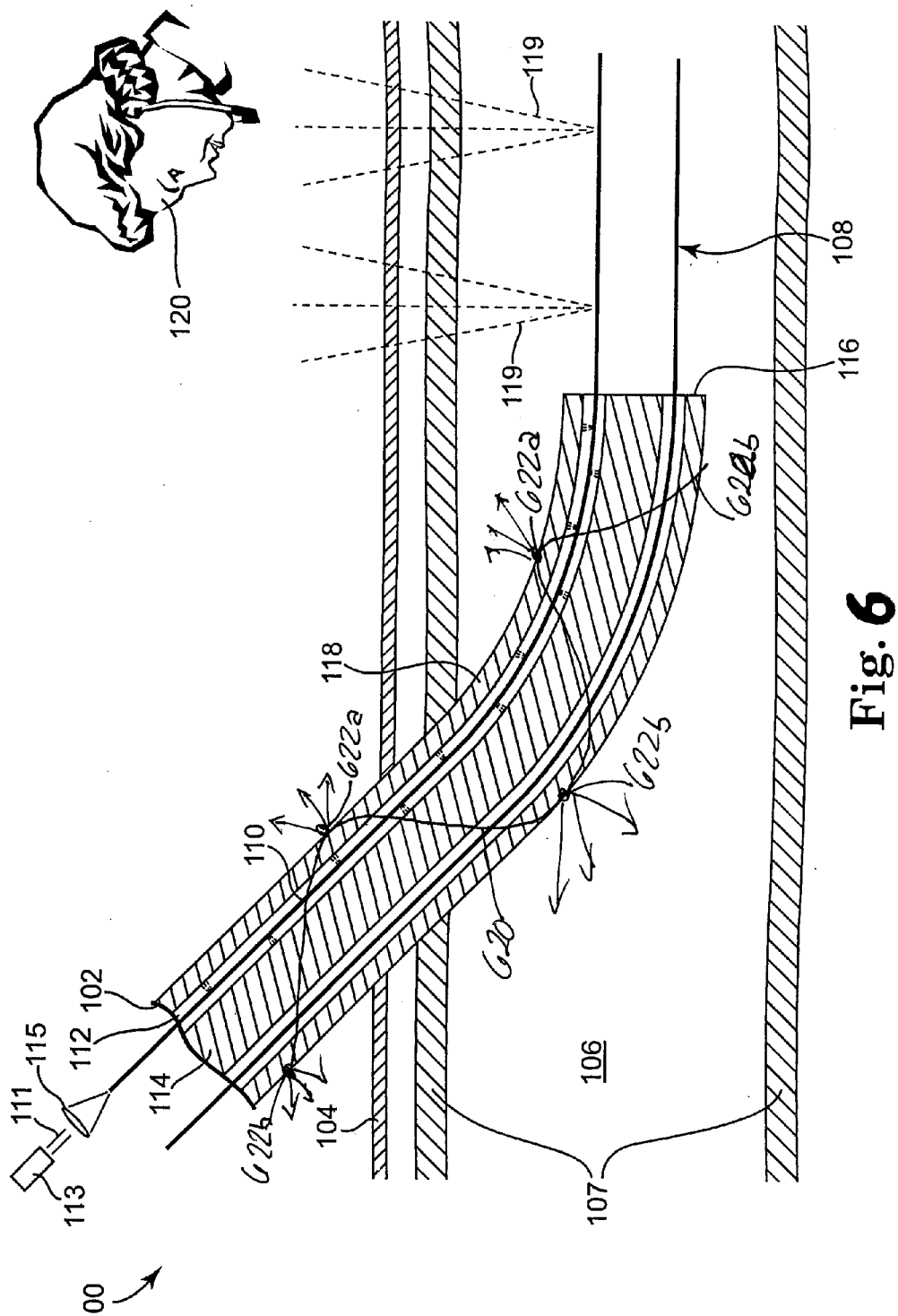
FIG. 6 is a view like FIG. 1 except showing a spiral wound light source.
Figure 7:
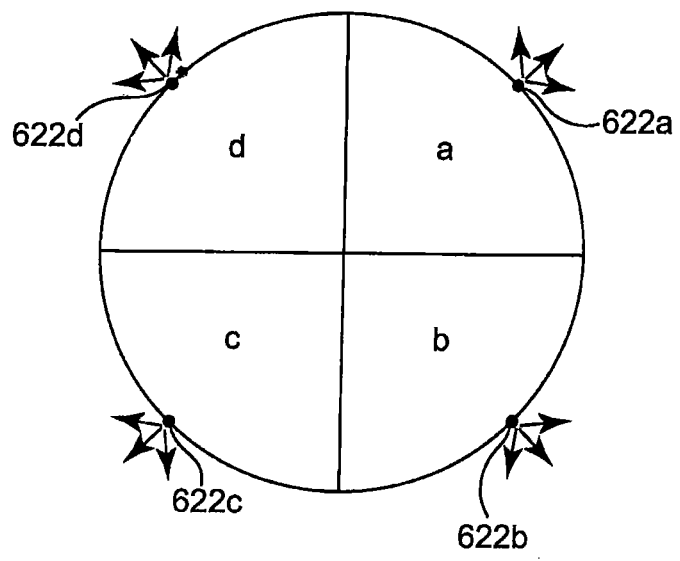
FIG. 7 is a schematic cross sectional view of FIG. 6 but limited to the spiral wound light source winding.

It is possible to wind the fibers along catheter in a helical or spiral 620 with illumination point 622*a-b-c-d* as shown in FIG. 6 and FIG. 7 showing a cross sectional schematic view of the quadrants and point light sources 622*a-d*. This will make it possible to know the orientation of the catheter along its length. This is accomplished by using different colored light sources along different sides (quadrants) of the cylindrical catheter wall. If the exterior wall is seen to have quadrants (for example, 4 circumferential sectors), the colors which align at each sector could be the same. If blue is used in sector 1, it will repeat when the spiral point illumination appears in that sector again. This helical illumination system could also be combined with multicolor illumination to have each side (for example 90 degrees) of rotation have a series of point light sources of the same color so it would be easy to discern which side of the catheter is facing upward.

Another solution to the heat reduction problem caused by illumination (or other heat sources introduced into the lumens), is to use various forms of heat sinking in one of the lumens. For example, a chilled rod may be introduced into one of the lumens in order to continuously withdraw heat. The chilling can be external, such as liquid nitrogen, other forms of refrigeration, or by solid state cooling as known in the art.

A heat sinking spiral wound wire (preferably under the cladding) can also be used to withdraw heat similar to wire 620.

Illumination of tip 650 of the catheter (FIG. 8) can be made with a point source LED or merely the end of a fiber optic. It can have an omnidirectional output (forward and orthogonal to the catheter direction), but it could also be unidirectional, preferably orthogonal to the direction of catheter. This would be particularly helpful where a remotely steerable/guidable catheter is used since the tip will illuminate strongest when pointing upwardly toward the external viewer (user). Combining this technique with multicolored illumination points, the tip could have a plurality (preferably 4 quadrants) of point illumination. The user could tell by color which direction the tip was pointing. This will make it possible to see the end with lower heat output. The preferred construction is at least 4 LED or fiber optic points, orthogonal to the longitudinal direction, similar to that shown in FIG. 7 with points 622*a-d*.

With illumination at the tip (or extra bright illumination at the tip) the user can more easily guide the travel of the catheter in a manner similar to that used with radio opaque catheters which can be monitored by a fluoroscope. With this technique of mere illumination, the patient avoids dangerous irradiation. There are many possible uses for such a construction: placement in the stomach, in the heart etc. In newborns and infants, I have found that it is quite possible to see visible light fairly deep within the body, without the need for Xray fluoroscopy. Nevertheless, the present invention can be combined with known radio opaque techniques to make the catheter visible both optically and by radio detectors.

Ultrasonic identification can also be included by using materials which provide identifiable signatures to ultrasound interrogation, or by emitting sound in a similar manner as described above for light (e.g., pulsatile discrete points).

Likewise, radio-frequency identification (RFID) can be embedded into the catheter in locations therealong much like LEDs so that the visual image can be supplemented with RFID location information. By using serialized RFIDs spaced along the length of the catheter, a detector can provide additional location information, for example, at the tip.

In addition to locating the illumination points at the tip orthogonally, the tip may also be wedge shaped (see FIG. 9 with oblique angle), pointed or other formation which allows transmission of light generally orthogonally or at another angle.

Additional Therapeutic Uses

In addition to the above mentioned therapeutic uses of an illuminated catheter, it is possible to provide photo-therapeutic illumination within the body to treat certain conditions more effectively than by present external photo-therapeutic illumination.

One such example is the use of an illuminated catheter for transdermal visualization of tube thoracostomy placement (chest tube). The present invention (either single or several discrete points along the catheter and terminating at the tip which are illuminated continuously or with strobing/flashing) would show the course of the catheter tube and its tip location. The catheter can also be equipped with side holes for evacuation of air or liquids. Point of light emission could also indicate the location of these side, as all of these must reside inside the chest cavity for the suction to be effective. This tube is placed through the chest wall into the space between the lung and ribs and attached to suction in order to evacuate air or fluid. In order to be effective, proper anterior (above the lung) placement for air evacuation, or proper posterior (below the lung) placement for fluid evacuation is crucial. Immediate recognition of actual tip localization at the anterior (front) or posterior (back) of the chest wall is essential and can be lifesaving. Traditionally, x-ray has been used to locate radio opaque catheter, but the response time to set up is too slow. It is important to get the tube inserted quickly. With the present invention, the illumination will be visible from the posterior or anterior, confirming to the user that it is in front of or behind the lung.

Another use of the present invention is for use of an illuminated catheter for transdermal visualization of nasogastric or orogastric tube placement. These are feeding tubes that are introduced through the nose or mouth and advanced so that the tip lies in the stomach. With the present invention, this process can be viewed in real-time similar to that of PICC placement. Sedated patients, which are the predominate population across all ages in intensive care units, are at a significantly increased risk for incorrect feeding tube placement. Errant placement into the trachea and/or lung can be fatal and should be preventable by this strategy. In addition, migration of the tube over time into the esophagus can place the patient at increased risk for vomiting and aspiration into the lungs. The ability to check initial placement and to continue to validate tube position by direct viewing of the illumination source, on at least a daily basis without unnecessary radiation exposure is a benefit to the patient.

Another use of the present invention is use of an illuminated catheter for transdermal visualization of umbilical arterial and umbilical venous line placement in neonates. These long catheters provide newborn babies with lifesaving nutrition and arterial blood access with continuous blood pressure monitoring. The location of the catheters during placement would be easily observed in real time by the unaided naked eye by virtue of the illuminated catheter, in a manner similar to that described for the other intravenous/intraarterial catheters. As the umbilical venous catheters often curve or divert into the liver, this would be immediately recognizable and correctable in neonates without having to wait for an Xray to be taken and processed (up to an hour later).

For example, the standard treatment of bilirubin is to flood the patient (infant) with phototherapy-UV radiation (350 nM for example) by means of overhead lighting. This requires the patient to be exposed to the air, and consequential heat loss, evaporation, and requires the patient to have eye protection. Furthermore, the entire skin surface is receiving UV radiation, whereas only the bilirubin component in the blood needs such treatment. By placement of an illuminated catheter or other tubular element, built according to the present disclosure at a location likely to encounter substantial blood flow and supplying UV frequency illumination to the tubular element, bilirubin can be treated from the "inside out" without other consequences of UV exposure. Typically that means threading the catheter near the heart and supplying UV light thru the fiber optic or through one of the lumens or by other means described herein. It would be possible to use one of the lumen channels to make real time readings of bilirubin levels so that the illumination can be terminated as soon as it is unneeded.

Further therapeutic uses of the catheter are also possible by moving the fiber optic/LED or other illumination from one of the lumens to just under the protective sheath/cover 118. The cover is either transparent or translucent to conduct light, where the fiber is placed immediately under the cover. This frees up one of the lumens (or allows for small diameter catheters). If lossy optical fibers are used, they may preferably be spiral wound similar to that shown in FIG. 6 except preferably covering the entire tubular surface for maximum illumination.

As mentioned above, it is also possible to embed various sensors into the catheter to allow real time readings to be made while supplying other fluids in the open lumens.

A further "smart" version of the catheter is possible where the same optical fiber which supplies illumination is bidirectional and possibly with a dichroic mirror can receive reflected illumination and, for example, locate blood vessels not visible from the surface. Likewise blood gasses, blood pressure, electrical conductivity or current flow (using special cladding) and other blood constituents can be monitored by sensor in the catheter or which are inserted according to need down one of the lumens.

The power source for illumination can be external to the catheter or with low power illumination sources, such as LEDs. The power source may be encapsulated into the proximal (user) end. It should be possible to get several weeks of intermittent illumination from a few wrist watch battery equivalents.

It is also possible to combine any or all of the features of the present invention with steerability. An example of a steerable catheter is found in U.S. Pat. No. 5,342,300 which is herein incorporated by reference and details a structure to steer a catheter. By combining this feature with illumination capability the user can achieve positioning of the catheter in specific locations without the need for dangerous radiation streaming into the body during placement. This could be coupled with an oblique optic tip such as in FIG. 9 which would enable coordinated bending/steering of the catheter in the direction of the oblique fiber face. This could be made apparent to the operator by rotating the catheter to the angle of maximum light signal, indicating that the bend would then be toward the operator.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

I claim:

1. A transcutaneously viewable catheter comprising:
   a) an elongated tubular member having a proximal end and a distal end and a first channel that extends from the proximal end to the distal end of the tubular member; and
   b) a single elongated optical fiber disposed within the first channel and having a proximal end, a distal end, and a peripheral surface on a cladding of the optical fiber, wherein the optical fiber comprises a plastic or polymer, wherein the peripheral surface of the optical fiber comprises two or more discrete illumination points spaced apart along the optical fiber to create an optical path for exit of light through the cladding from a core within the optical fiber such that during use in a subject the exiting light is visible outside the subject's body to an unaided eye,
   wherein the discrete illumination points comprise heat deformations applied to the cladding of the optical fiber, wherein the heat deformations have a depth less than a radius of the optical fiber, and (i) the deformations are spaced progressively closer together or progressively farther apart towards the distal end of the optical fiber, or (ii) the deformations are progressively larger towards the distal end of the optical fiber, or both (i) and (ii), and
   wherein the optical fiber is configured so that during use light exits from a tip of the distal end and is visible outside the subject's body with the unaided eye.

2. The catheter of claim 1, wherein a plurality of the discrete illumination points are spaced along the optical fiber to illuminate the catheter periodically at varying points around a circumference of the tubular member, so that all sides of the catheter are illuminated by the plurality of discrete illumination points from proximal to distal ends.

3. The catheter of claim 1, further including a heat sink in the tubular member and extending generally the length thereof.

4. The catheter of claim 1, wherein the deformations are heat or laser cuts in the peripheral surface of the optical fiber.

5. The catheter of claim 1, wherein the deformations are formed by heat or laser etching the peripheral surface of the optical fiber.

6. The catheter of claim 1, wherein the tip of the distal end is illuminated by a directional point source that emits in a direction that is generally orthogonal to a longitudinal axis of the catheter, so that the orientation of the tip of the distal end can be known by visualization of the directional point source by a user.

7. The catheter of claim 1, wherein the tubular member is at least partially transparent to light emitted by the optical fiber; so that when the optical fiber reaches the end of tubular member, an observer can detect a difference in level, pattern, or wavelength of light transmission as the optical fiber exits the tubular member.

8. The catheter of claim 1, further comprising a light emitting device, wherein the light emitting device, the optical fiber, and the catheter are configured to cause the optical fiber to emit light of a different intensity, pattern, or wavelength at the distal end of the optical fiber than elsewhere therealong, so that in use in a subject it is possible to easily discern a path and distal end of the optical fiber from outside the subject's body.

9. The catheter of claim 1, further comprising a light emitting device, wherein the light emitting device is configured to emit light of a predetermined optical-wavelength(s) to excite fluorescence from blood constituents; an optical channel to receive fluorescence from blood constituents; and an optical detector coupled to the optical channel to measure fluorescence from blood constituents.

10. The catheter of claim 1, wherein the deformations are spaced progressively closer together as the illumination points approach the distal end of the optical fiber.

11. The catheter of claim 1, wherein the deformations are filled with a translucent lens material.

12. The catheter of claim 11, wherein said lens material includes suspended reflective particles.

13. The catheter of claim 12, wherein the particles are powdered silver.

14. The catheter of claim 11, wherein a lens dome filler fills the deformations and creates a diffusing or focusing lens thereon.

15. The catheter of claim 1, wherein the deformations are progressively deeper or wider towards the distal end so as to allow a similar amount of light to be emitted from each deformation along the optical fiber.

16. The catheter of claim 1, wherein the distal end is at least partially reflective such that at least some of the light reaching the distal end is reflected backward and may exit the discrete illumination points, thereby adding light intensity exiting from the discrete illumination points.

17. The catheter of claim 1, wherein the discrete illumination points are located at points circumferentially around the optical fiber.

18. The catheter of claim 1, wherein the discrete illumination points are located at points generally 120 degrees of rotation apart along a circumferential surface of the optical fiber.

19. The catheter of claim 1, wherein the discrete illumination points are circumferential around a periphery of the optical fiber thereby forming bands.

20. The catheter of claim 1, further comprising a light emitting device wherein the light emitting device, the optical fiber, and the catheter are configured to cause light that exits the catheter at locations corresponding to the discrete illumination points to be modulated to be progressively brighter toward the distal end of the illumination source.

21. The catheter of claim 1, further comprising a light emitting device wherein the light emitting device, the optical fiber, and the catheter are configured to cause light that exits the catheter at locations corresponding to the discrete illumination points to have a greater intensity progressively toward the distal end of the illumination source.

22. The catheter of claim 1, further comprising a light emitting device wherein the light emitting device, the optical fiber, and the catheter are configured to cause light that exits the catheter at locations corresponding to the discrete illumination points to be modulated at a first frequency and light that exits from the tip at the distal end to be modulated at a second frequency different from the first frequency.

23. The catheter of claim 1, wherein the heat deformations are laser burns.

24. The catheter of claim 1, wherein the heat deformations are heated wire burns.

25. The catheter of claim 1, further including a first light emitting device that illuminates the optical fiber with light of a first wavelength.

26. The catheter of claim 25, further including a second light emitting device and a second optical fiber, wherein the second light emitting device illuminates the second optical fiber with light of a different wavelength than the first light emitting device, so that in use in a subject a depth of the catheter within the subject can be ascertained by the relative adsorption of the two wavelengths through the subject's tissue.

27. The catheter of claim 26, wherein the first and second optical fibers are both disposed within the first channel.

28. The catheter of claim 1, wherein the heat deformations are formed in the cladding and at least a portion of the core of the optical fiber.

* * * * *